United States Patent
Koo et al.

(10) Patent No.: US 11,629,321 B2
(45) Date of Patent: Apr. 18, 2023

(54) SCAFFOLD FOR CELL CULTURE OR TISSUE ENGINEERING

(71) Applicant: AMOLIFESCIENCE CO., LTD., Seoul (KR)

(72) Inventors: Song Hee Koo, Gimpo-si (KR); Seon Ho Jang, Seoul (KR); In Yong Seo, Seoul (KR); Chan Kim, Gwangju (KR); Seoung Hoon Lee, Paju-si (KR); Yun Mi So, Incheon (KR); Ji Hyun Lee, Incheon (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 1051 days.

(21) Appl. No.: 16/305,231

(22) PCT Filed: May 31, 2017

(86) PCT No.: PCT/KR2017/005705
§ 371 (c)(1),
(2) Date: Nov. 28, 2018

(87) PCT Pub. No.: WO2017/209521
PCT Pub. Date: Dec. 7, 2017

(65) Prior Publication Data
US 2020/0318049 A1    Oct. 8, 2020

(30) Foreign Application Priority Data

May 31, 2016    (KR) .................. 10-2016-0067715
May 31, 2016    (KR) .................. 10-2016-0067728

(51) Int. Cl.
C12M 1/12    (2006.01)
C12M 1/04    (2006.01)
(Continued)

(52) U.S. Cl.
CPC ............ *C12M 25/14* (2013.01); *C12M 23/24* (2013.01); *D01D 5/003* (2013.01); *D01F 6/12* (2013.01);
(Continued)

(58) Field of Classification Search
CPC ....... C12M 25/14; C12M 23/24; D01D 5/003; D01F 6/12; D04H 1/728; D10B 2321/042
(Continued)

(56) References Cited

U.S. PATENT DOCUMENTS

2011/0250689 A1* 10/2011 Baaijens ............ D04H 1/43838
                                                          428/364
2013/0178949 A1*  7/2013 Bowlin ................ D04H 1/728
                                                          623/23.72

FOREIGN PATENT DOCUMENTS

CN    105238735    1/2016
KR    100875189    12/2008
(Continued)

OTHER PUBLICATIONS

Loh and Choong, Three-Dimensional Scaffolds for Tissue Engineering Applications: Role of Porosity and Pore Size, Tissue Engineering: Part B, vol. 19, No. 6 2013 (Year: 2013).*
(Continued)

*Primary Examiner* — Michael L Hobbs
*Assistant Examiner* — Lenora A Abel
(74) *Attorney, Agent, or Firm* — Cantor Colburn LLP

(57) ABSTRACT

A scaffold for cell culture or tissue engineering is provided. The scaffold includes a fiber web having a three-dimensional network structure, which includes a biodegradable scaffold fiber. Therefore, a microenvironment suitable for migration, proliferation and differentiation of cells to be cultured is created, thereby improving a cell proliferation rate and cell viability. In addition, the scaffold may be easily removed
(Continued)

from cells cultured therein without physical/chemical stimuli, and thus the cultured cells may be easily recovered, and is able to be grafted into the body while the cultured cells are included in the scaffold. Moreover, the cultured cells may be cultured to have a similar shape/structure to those of an actual animal body to make it more suitable to be applied in grafting into an in vitro experimental model or animal body.

12 Claims, 7 Drawing Sheets

Specification includes a Sequence Listing.

(51) Int. Cl.
    *D01D 5/00*     (2006.01)
    *D01F 6/12*     (2006.01)
    *D04H 1/728*     (2012.01)

(52) U.S. Cl.
    CPC ....... *D04H 1/728* (2013.01); *D10B 2321/042* (2013.01)

(58) Field of Classification Search
    USPC ...................................................... 435/297.1
    See application file for complete search history.

(56) References Cited

FOREIGN PATENT DOCUMENTS

| | | |
|---|---|---|
| KR | 20080104932 | 12/2008 |
| KR | 20100000289 | 1/2010 |
| KR | 101104305 | 1/2012 |
| KR | 20120097948 | 9/2012 |
| WO | 2016013848 | 1/2016 |

OTHER PUBLICATIONS

International Search Report—PCT/KR2017/005705 dated Sep. 12, 2017.
Sisson, et al., Fiber Diameters Control Osteoblastic Cell Migration and Differentiation in Electrospun Gelatin, Journal of Biomedical Materials Research Part A, Sep. 2010, pp. 1312-1320.

* cited by examiner

```
                     SEQUENCE LISTING

<160> NUMBER OF SEQ ID NOS: 28

<210> SEQ ID NO 1
<211> LENGTH: 196
<212> TYPE: PRT
<213> ORGANISM: Artificial Sequence
<220> FEATURE:
<223> OTHER INFORMATION: Motif for cell culture scaffold

<400> SEQUENCE: 1

Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
            20                  25                  30

Lys Pro Ser Tyr Pro Pro Thr Tyr Lys Ala Lys Pro Ser Tyr Pro Pro
        35                  40                  45

Thr Tyr Lys Ala Lys Pro Ser Tyr Pro Pro Thr Tyr Lys Ser Ser Glu
    50                  55                  60

Glu Tyr Lys Gly Gly Tyr Tyr Pro Gly Asn Thr Tyr His Tyr His Ser
65                  70                  75                  80

Gly Gly Ser Tyr His Gly Ser Gly Tyr His Gly Gly Tyr Lys Gly Lys
                85                  90                  95

Tyr Tyr Gly Lys Ala Lys Lys Tyr Tyr Tyr Lys Tyr Lys Asn Ser Gly
                100                 105                 110

Lys Tyr Lys Tyr Leu Lys Lys Ala Arg Lys Tyr His Arg Lys Gly Tyr
            115                 120                 125

Lys Lys Tyr Tyr Gly Gly Ser Ser Ala Lys Pro Ser Tyr Pro Pro Thr
    130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
                165                 170                 175

Ala Lys Pro Ser Tyr Pro Pro Thr Tyr Lys Ala Lys Pro Ser Tyr Pro
            180                 185                 190

Pro Thr Tyr Lys
            195

<210> SEQ ID NO 2
<211> LENGTH: 202
<212> TYPE: PRT
<213> ORGANISM: Artificial Sequence
<220> FEATURE:
<223> OTHER INFORMATION: Motif for cell culture scaffold
```

```
<400> SEQUENCE: 2

Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
            20                  25                  30

Lys Pro Ser Tyr Pro Pro Thr Tyr Lys Ala Lys Pro Ser Tyr Pro Pro
        35                  40                  45

Thr Tyr Lys Ala Lys Pro Ser Tyr Pro Pro Thr Tyr Lys Ser Ser Glu
    50                  55                  60

Glu Tyr Lys Gly Gly Tyr Tyr Pro Gly Asn Thr Tyr His Tyr His Ser
65                  70                  75                  80

Gly Gly Ser Tyr His Gly Ser Gly Tyr His Gly Gly Tyr Lys Gly Lys
                85                  90                  95

Tyr Tyr Gly Lys Ala Lys Lys Tyr Tyr Lys Tyr Lys Asn Ser Gly
                100                 105                 110

Lys Tyr Lys Tyr Leu Lys Lys Ala Arg Lys Tyr His Arg Lys Gly Tyr
                115                 120                 125

Lys Lys Tyr Tyr Gly Gly Ser Ser Ala Lys Pro Ser Tyr Pro Pro Thr
130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
                165                 170                 175

Ala Lys Pro Ser Tyr Pro Pro Thr Tyr Lys Ala Lys Pro Ser Tyr Pro
            180                 185                 190

Pro Thr Tyr Lys Gly Arg Gly Asp Ser Pro
            195                 200

<210> SEQ ID NO 3
<211> LENGTH: 172
<212> TYPE: PRT
<213> ORGANISM: Artificial Sequence
<220> FEATURE:
<223> OTHER INFORMATION: Motif for cell culture scaffold

<400> SEQUENCE: 3

Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
            20                  25                  30

Lys Pro Ser Tyr Pro Pro Thr Tyr Lys Ala Lys Pro Ser Tyr Pro Pro
        35                  40                  45

Thr Tyr Lys Ala Lys Pro Ser Tyr Pro Pro Thr Tyr Lys Pro Trp Ala
    50                  55                  60

Asp Tyr Tyr Gly Pro Lys Tyr Gly Pro Pro Arg Arg Tyr Gly Gly Gly
65                  70                  75                  80

Asn Tyr Asn Arg Tyr Gly Arg Arg Tyr Gly Tyr Lys Gly Trp Asn
                85                  90                  95

Asn Gly Trp Lys Arg Gly Arg Trp Gly Arg Lys Tyr Tyr Gly Ser Ala
                100                 105                 110

Lys Pro Ser Tyr Pro Pro Thr Tyr Lys Ala Lys Pro Ser Tyr Pro Pro
            115                 120                 125

Thr Tyr Lys Ala Lys Pro Ser Tyr Pro Pro Thr Tyr Lys Ala Lys Pro
        130                 135                 140
```

```
Ser Tyr Pro Pro Thr Tyr Lys Ala Lys Pro Ser Tyr Pro Pro Thr Tyr
145                 150                 155                 160

Lys Ala Lys Pro Ser Tyr Pro Pro Thr Tyr Lys Leu
            165                 170

<210> SEQ ID NO 4
<211> LENGTH: 46
<212> TYPE: PRT
<213> ORGANISM: Artificial Sequence
<220> FEATURE:
<223> OTHER INFORMATION: Motif for cell culture scaffold

<400> SEQUENCE: 4

Ala Asp Tyr Tyr Gly Pro Lys Tyr Gly Pro Pro Arg Arg Tyr Gly Gly
1               5                   10                  15

Gly Asn Tyr Asn Arg Tyr Gly Arg Arg Tyr Gly Gly Tyr Lys Gly Trp
            20                  25                  30

Asn Asn Gly Trp Lys Arg Gly Arg Trp Gly Arg Lys Tyr Tyr
            35                  40                  45

<210> SEQ ID NO 5
<211> LENGTH: 76
<212> TYPE: PRT
<213> ORGANISM: Artificial Sequence
<220> FEATURE:
<223> OTHER INFORMATION: Motif for cell culture scaffold

<400> SEQUENCE: 5

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Lys Tyr Lys
            35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser
65                  70                  75

<210> SEQ ID NO 6
<211> LENGTH: 10
<212> TYPE: PRT
<213> ORGANISM: Artificial Sequence
<220> FEATURE:
<223> OTHER INFORMATION: Motif for cell culture scaffold

<400> SEQUENCE: 6

Ala Lys Pro Ser Tyr Pro Pro Thr Tyr Lys
1               5                   10

<210> SEQ ID NO 7
<211> LENGTH: 60
<212> TYPE: PRT
<213> ORGANISM: Artificial Sequence
<220> FEATURE:
<223> OTHER INFORMATION: Motif for cell culture scaffold

<400> SEQUENCE: 7

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30
```

```
Pro Ser Tyr Pro Pro Thr Tyr Lys Ala Lys Pro Ser Tyr Pro Pro Thr
            35                  40                  45

Tyr Lys Ala Lys Pro Ser Tyr Pro Pro Thr Tyr Lys
 50                  55                  60

<210> SEQ ID NO 8
<211> LENGTH: 3
<212> TYPE: PRT
<213> ORGANISM: Artificial Sequence
<220> FEATURE:
<223> OTHER INFORMATION: Motif for cell culture scaffold

<400> SEQUENCE: 8

Arg Gly Asp
1

<210> SEQ ID NO 9
<211> LENGTH: 4
<212> TYPE: PRT
<213> ORGANISM: Artificial Sequence
<220> FEATURE:
<223> OTHER INFORMATION: Motif for cell culture scaffold

<400> SEQUENCE: 9

Arg Gly Asp Ser
1

<210> SEQ ID NO 10
<211> LENGTH: 4
<212> TYPE: PRT
<213> ORGANISM: Artificial Sequence
<220> FEATURE:
<223> OTHER INFORMATION: Motif for cell culture scaffold

<400> SEQUENCE: 10

Arg Gly Asp Cys
1

<210> SEQ ID NO 11
<211> LENGTH: 4
<212> TYPE: PRT
<213> ORGANISM: Artificial Sequence
<220> FEATURE:
<223> OTHER INFORMATION: Motif for cell culture scaffold

<400> SEQUENCE: 11

Arg Gly Asp Val
1

<210> SEQ ID NO 12
<211> LENGTH: 10
<212> TYPE: PRT
<213> ORGANISM: Artificial Sequence
<220> FEATURE:
<223> OTHER INFORMATION: Motif for cell culture scaffold

<400> SEQUENCE: 12

Arg Gly Asp Ser Pro Ala Ser Ser Lys Pro
1               5                   10

<210> SEQ ID NO 13
<211> LENGTH: 5
<212> TYPE: PRT
<213> ORGANISM: Artificial Sequence
<220> FEATURE:
<223> OTHER INFORMATION: Motif for cell culture scaffold
```

<400> SEQUENCE: 13

Gly Arg Gly Asp Ser
1               5

<210> SEQ ID NO 14
<211> LENGTH: 6
<212> TYPE: PRT
<213> ORGANISM: Artificial Sequence
<220> FEATURE:
<223> OTHER INFORMATION: Motif for cell culture scaffold

<400> SEQUENCE: 14

Gly Arg Gly Asp Thr Pro
1               5

<210> SEQ ID NO 15
<211> LENGTH: 6
<212> TYPE: PRT
<213> ORGANISM: Artificial Sequence
<220> FEATURE:
<223> OTHER INFORMATION: Motif for cell culture scaffold

<400> SEQUENCE: 15

Gly Arg Gly Asp Ser Pro
1               5

<210> SEQ ID NO 16
<211> LENGTH: 7
<212> TYPE: PRT
<213> ORGANISM: Artificial Sequence
<220> FEATURE:
<223> OTHER INFORMATION: Motif for cell culture scaffold

<400> SEQUENCE: 16

Gly Arg Gly Asp Ser Pro Cys
1               5

<210> SEQ ID NO 17
<211> LENGTH: 5
<212> TYPE: PRT
<213> ORGANISM: Artificial Sequence
<220> FEATURE:
<223> OTHER INFORMATION: Motif for cell culture scaffold

<400> SEQUENCE: 17

Tyr Arg Gly Asp Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Motif for cell culture scaffold

<400> SEQUENCE: 18

Ser Pro Pro Arg Arg Ala Arg Val Thr
1               5

<210> SEQ ID NO 19
<211> LENGTH: 8
<212> TYPE: PRT
<213> ORGANISM: Artificial Sequence
<220> FEATURE:
<223> OTHER INFORMATION: Motif for cell culture scaffold

<400> SEQUENCE: 19

Trp Gln Pro Pro Arg Ala Arg Ile
1               5

<210> SEQ ID NO 20
<211> LENGTH: 12
<212> TYPE: PRT
<213> ORGANISM: Artificial Sequence
<220> FEATURE:
<223> OTHER INFORMATION: Motif for cell culture scaffold

<400> SEQUENCE: 20

Asn Arg Trp His Ser Ile Tyr Ile Thr Arg Phe Gly
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Motif for cell culture scaffold

<400> SEQUENCE: 21

Arg Lys Arg Leu Gln Val Gln Leu Ser Ile Arg Thr
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Motif for cell culture scaffold

<400> SEQUENCE: 22

Lys Ala Phe Asp Ile Thr Tyr Val Arg Leu Lys Phe
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Motif for cell culture scaffold

<400> SEQUENCE: 23

Ile Lys Val Ala Asn
1               5

<210> SEQ ID NO 24
<211> LENGTH: 16
<212> TYPE: PRT
<213> ORGANISM: Artificial Sequence
<220> FEATURE:
<223> OTHER INFORMATION: Motif for cell culture scaffold

<400> SEQUENCE: 24

Lys Lys Gln Arg Phe Arg His Arg Asn Arg Lys Gly Tyr Arg Ser Gln
1               5                   10                  15

<210> SEQ ID NO 25
<211> LENGTH: 9
<212> TYPE: PRT
<213> ORGANISM: Artificial Sequence

```
<220> FEATURE:
<223> OTHER INFORMATION: Motif for cell culture scaffold

<400> SEQUENCE: 25

Val Ala Glu Ile Asp Gly Ile Gly Leu
1               5

<210> SEQ ID NO 26
<211> LENGTH: 10
<212> TYPE: PRT
<213> ORGANISM: Artificial Sequence
<220> FEATURE:
<223> OTHER INFORMATION: Motif for cell culture scaffold

<400> SEQUENCE: 26

Pro His Ser Arg Asn Arg Gly Asp Ser Pro
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Motif for cell culture scaffold

<400> SEQUENCE: 27

Asn Arg Trp His Ser Ile Tyr Ile Thr Arg Phe Gly
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Motif for cell culture scaffold

<400> SEQUENCE: 28

Thr Trp Tyr Lys Ile Ala Phe Gln Arg Asn Arg Lys
1               5                   10
```

SCAFFOLD FOR CELL CULTURE OR TISSUE ENGINEERING

TECHNICAL FIELD

The present invention relates to a scaffold, and more particularly, to a scaffold for cell culture or tissue engineering which enhances cell viability by creating a microenvironment suitable for migration, proliferation and differentiation of cells to be cultured and facilitates isolation of the cultured cells.

BACKGROUND ART

Recently, according to expansion of the use of cultured cells in disease treatment, interest in and research on cell culture are increasing. Cell culture is a technique for collecting cells from a living organism and culturing the cells outside the living organism, and the cultured cells may be used in treatment of various diseases through differentiation into various types of tissue of a body, for example, the skin, organs, nerves, etc. to be grafted into the body, or grafting in an undifferentiated state to attain engraftment and differentiation at the same time.

A field associated with such cell culture is tissue engineering, which is an interdisciplinary study that applies existing scientific fields such as cytology, life science, engineering, medicine, etc., and thus novel fusion technology for understanding a relationship between the structure and function of living tissue, replacing damaged tissue or a damaged organ with normal tissue and regenerating the damaged tissue or organ has been studied.

Such fusion technology is continuously receiving a great deal of attention in a conventional cell culture field or a tissue engineering field using the same, and one of tasks which are being studied and developed is a study of a material or structure of a scaffold which can culture/differentiate cells and be implanted into human tissue while including the cells. That is, to examine an influence of a specific material on the human body, a toxicity experiment for the specific material using cultured cells may be more suitable as an in vitro cytotoxicity test model that is similar to an actual human cell structure, compared with that performed using a cell cluster cultured/distributed in a three-dimensional structure, which is similar to the actual human cell structure. In addition, to graft cultured cells into human tissue, cells or tissue grafted when a cell cluster cultured/differentiated in a three-dimensional structure similar to the actual human tissue may play a sufficient function and role.

However, since cells are not cultured in scaffolds for cell culture, that have been developed so far, that have a similar structure to that in a body, cell viability is not high, and therefore the cultured cells are inappropriate as an in vitro experimental model or cells for grafting.

For this reason, there is an urgent demand for development of a scaffold which can provide culture environments similar to the human body, ensure a proper space required for cell culture and prevent detachment of cells from the scaffold during culture to increase cell viability and three-dimensionally grow the cells.

DISCLOSURE

Technical Problem

The present invention is devised by taking the above-mentioned problems into account, and thus directed to providing a scaffold for cell culture or tissue engineering which improves a cell proliferation rate and cell viability by creating a microenvironment suitable for migration, proliferation and differentiation of cells to be cultured.

In addition, the present invention is also directed to providing a scaffold for cell culture or tissue engineering which can be easily removed from cells cultured therein without physical/chemical stimuli, and thus the cultured cells can be easily recovered.

In addition, the present invention is also directed to providing a scaffold which is more suitably formed for the purposes of cell culture and tissue engineering since it is grafted into a body with cells.

In addition, the present invention is also directed to providing a scaffold which can culture cells to have a similar shape/structure to those actually in an animal body such that the cultured cells can be suitable for being applied in grafting into in vitro experimental model or an animal body.

In addition, the present invention is also directed to providing a scaffold which can be applied in production of various types of products used in a cell culture or tissue engineering field, including a bioreactor, a cell incubator, a grafting kit, etc.

Technical Solution

To solve the above-described problems, the present invention provides a scaffold for cell culture or tissue engineering, which includes a fiber web with a three-dimensional structure, including a scaffold fiber.

According to an exemplary embodiment of the present invention, the fiber web may have an average pore size of 0.05 to 10 μm and a porosity of 40 to 90%.

In addition, the scaffold fiber may have an average diameter of 100 nm to 3 μm.

In addition, the fiber web may have a thickness of 1 to 20 μm and a basis weight of 1 to 30 g/m².

In addition, the fiber web may include a plurality of scaffold fibers, and satisfy Conditions (1) and (2): (1) a diameter dispersion coefficient (E) is 8 to 25% in the diameter distribution of the scaffold fibers, and (2) the air permeability of the fiber web is 1 to 40 cfm.

In addition, as Condition (3) for the diameter distribution of the scaffold fibers, a value according to Mathematical Formula 1 below may be 1.5 to 6.8.

[Mathematical Formula 1]

$$\frac{\text{Maximum diamter (nm)} - \text{Third quartile (nm)}}{\text{Third quartile (nm)} - \text{First quartile (nm)}}$$

In addition, as Condition (4) for the diameter distribution of the scaffold fibers, a value according to Mathematical Formula 2 below may be 1.0 to 5.5.

[Mathematical Formula 2]

$$\frac{\text{First quartile (nm)} - \text{Minimum diameter (nm)}}{\text{Third quartile (nm)} - \text{First quartile (nm)}}$$

In addition, the scaffold fiber may include any one or more biodegradable components selected from the group consisting of polycaprolactone (PCL), polydioxanone (PDO), poly(L-lactide) (PLLA), poly(DL-lactide-co-glycolide) (PLGA), polyethylene oxide (PEO), polylactic acid (PLA) and polyvinyl alcohol (PVA) as a fiber-forming component.

In addition, the scaffold fiber may include any one or more non-biodegradable components selected from the group consisting of polystyrene, polyethylene terephthalate (PET), polyethersulfone (PES), polyvinylidene fluoride (PVDF), polydimethylsiloxane (PDMS), a polyamide, polyethylene and a polyethyleneoxide-polypropyleneoxide block copolymer as a fiber-forming component.

In addition, the present invention provides a scaffold according to the present invention and a bioreactor including a housing having the scaffold.

In addition, the present invention provides a cell incubator including the scaffold according to the present invention.

In addition, the present invention provides a grafting kit, which includes a scaffold according to the present invention and a cell cluster cultured in outer and inner spaces of a fiber web of the scaffold.

Amino acid sequences used in the present invention are abbreviated according to the IUPAC-IUB nomenclature as shown in Table 1 below.

TABLE 1

| IUPAC-IUB name | Symbol | Simplified form |
| --- | --- | --- |
| Alanine | A | Ala |
| Arginine | R | Arg |
| Asparagine | N | Asn |
| Cysteine | C | Cyn |
| Glutamic acid | E | Glu |
| Glutamine | Q | Gln |
| Glycine | G | Gly |
| Histidine | H | His |
| Isoleucine | I | Ile |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Hereinafter, terms used herein will be described.

The term "extracellular matrix (ECM)" used herein is a substrate which surrounds the outside of a cell, occupies a space between cells, and has a network structure usually consisting of proteins and polysaccharides.

The "motif" used herein is a peptide comprising an amino acid sequence, which can structurally/functionally interact with a receptor included in a protein, a glucoprotein, etc. in the ECM playing a critical role in cell adhesion, migration, differentiation, etc. to pass through a surface of a cell membrane or a membrane, and is isolated from a cell or artificially produced using a gene cloning technique.

The term "three-dimensional cell cluster" used herein refers to a group of cells which are three-dimensionally gathered, and an artificially-formed cell cluster similar to tissue in a body due to cell-cell interactions caused by expression of a gap junction protein such as cadherin or connexin. The three-dimensional cell cluster includes a multilayer of cells, and the two-dimensional cell cluster is a single layer of cells, which means that the three-dimensional cell cluster has a larger number of cells per unit area than the two-dimensionally cultured cells.

Advantageous Effects

According to the present invention, a microenvironment suitable for the migration, proliferation and differentiation of cells to be cultured is created in a scaffold and thus a cell proliferation rate and cell viability may be enhanced. In addition, the scaffold can be easily removed without physical/chemical stimuli to cultured cells therein, and thus the cultured cells can be easily recovered and the scaffold can be grafted into a body with the cultured cells.

Further, the cultured cells can be cultured to have a shape/structure similar to the actual animal body such that the cells can be suitable for being applied in grafting into an in vitro experimental model or animal body.

In addition, the scaffold according to an exemplary embodiment of the present invention can be modified with a material that helps cell culture/differentiation such that cell proliferation and cell viability can be further improved, and the cultured cells can be easily grown in a three-dimensional shape. For this reason, the scaffold can be very suitable for being used in cell culture and tissue engineering fields, and thus can be widely applied to various products in the corresponding fields.

DESCRIPTION OF DRAWINGS

FIGS. 2A to 2D show a partially-enlarged cross-sectional view of a scaffold fiber included in an exemplary embodiment of the present invention in a major axis direction, in which FIGS. 2A to 2D show various exemplary embodiments for the arrangement of an adhesive physiologically active component and/or non-adhesive physiologically active component, which are included inside and outside the scaffold fiber.

FIGS. 3A and 3B show a scaffold fiber included in an exemplary embodiment of the present invention and an adhesive physiologically active component and a non-adhesive physiologically active component, which are included on the surface thereof, in which FIG. 3A is a partial perspective view showing that an adhesive physiologically active component is arranged on a part of the surface of a scaffold fiber and then a non-adhesive physiologically active component is fixed to the adhesive physiologically active component, and FIG. 3B is a cross-sectional view showing that the surface of a scaffold fiber is covered with an adhesive physiologically active component, and the coated adhesive physiologically active component is coated with a non-adhesive physiologically active component.

MODES OF THE INVENTION

Figure 1:
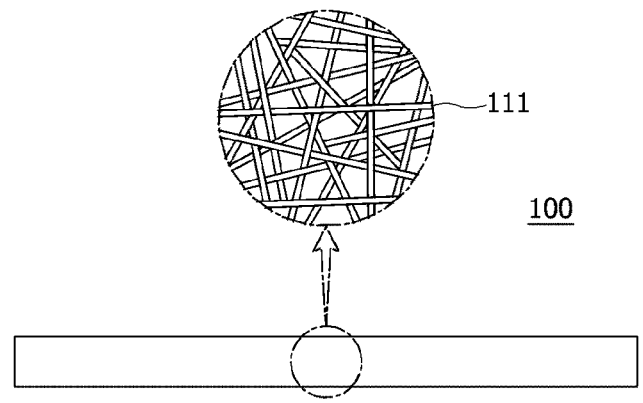
FIG. 1 shows a cross-sectional view and an enlargement of a fiber web included in a scaffold according to an exemplary embodiment of the present invention.

Hereinafter, embodiments of the present invention will be described in detail with reference to the accompanying drawings so that those of ordinary skill in the art can easily carry out the present invention. The present invention may be implemented in a variety of different forms, and is not limited to the embodiments described herein. For clear explanation of the present invention in the drawings, parts that are not related to the description are omitted, and the same numerals denote the same or like components throughout the specification.

Figure 2A:
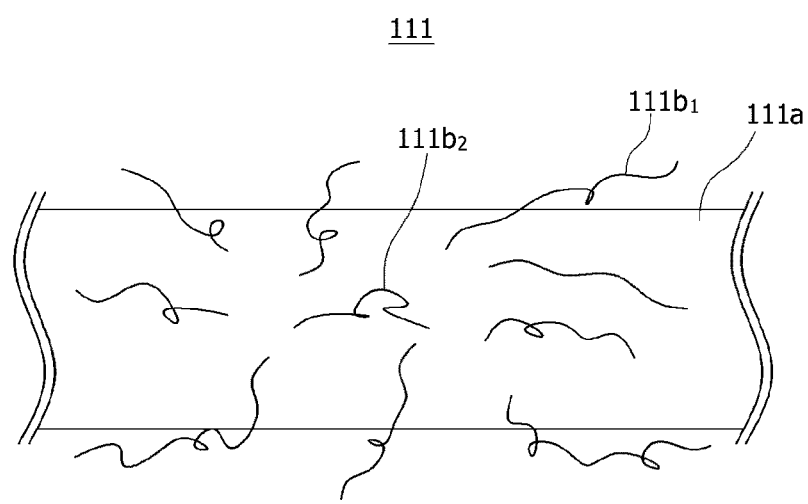

In addition, the present invention is not limited to the forms illustrated in the drawings. As an example, although physiologically active components shown in FIG. 2A, the adhesive physiologically active components $111b_1$ and $111b_2$ are illustrated like a thread, which is to be easy to explain a positional relationship between adhesive physiologically active components located outside/inside a fiber, they may be different from an actual shape of the adhesive physiologically active component. In addition, in the case of the adhesive physiologically active component illustrated in the form of a thread, as shown in FIG. 2A, it was shown that the adhesive physiologically active component $111b_1$ is detached from the outer surface of the scaffold fiber 111, but the present invention is not limited thereto, and it should be understood that the case in which the adhesive physiologically active component $111b_1$ is partially applied to the outer surface without being detached from the outer surface of the scaffold fiber 111 is included.

As shown in FIG. 1, a scaffold according to an exemplary embodiment of the present invention includes a fiber web 100 consisting of a scaffold fiber 111. The fiber web 100 may include at least one strand of the scaffold fiber and form a three-dimensional network structure. Specifically, the fiber web formed of one strand of the scaffold fiber may have a three-dimensional network structure by folding the strand of the scaffold fiber several times without orientation to arrange and stack.

In addition, the fiber web 100 may include multiple strands of the scaffold fibers, and each scaffold fiber is independently arranged/stacked without folding and/or determination of a fiber length direction, thereby forming a three-dimensional network structure. Here, adhesion or fusion may occur between different surfaces in one strand of the scaffold fiber and/or between surfaces of different scaffold fibers. Therefore, the three-dimensional network structure may become more complicated, cells loaded onto the scaffold may be migrated/proliferation into pores formed in the three-dimensional network structure, and it is advantageous for culturing cells as a cell cluster having a three-dimensional shape/structure.

In addition, to increase a proliferation rate and viability of cells cultured inside/outside the scaffold, it is important to supply nutrients required for cell proliferation, and the fiber web of the three-dimensional network structure has a variety of very complicated fluid channels through which a culture medium containing nutrients can pass to easily provide nutrients to cells located in the scaffold, such that cell death can be prevented and cell proliferation can be improved.

The pores in the fiber web 100 may have a diameter to ensure spaces in which cells can be migrated and proliferated, and since the diameter may be determined by a specific type of cells to be cultured, the average pore size is not particularly limited in the present invention. However, the average pore size is preferably 0.05 to 50 µm, and more preferably 0.05 to 10 µm. If the average pore size is less than 0.05 µm, during proliferation, the cells to be cultured may be two-dimensionally migrated and proliferated along the outer surface of the fiber web, rather than being migrated into pores in the fiber web, and therefore, a cell cluster having a three-dimensional shape may not be cultured at a desired level. In addition, although cells are migrated into the inner space of the fiber web, since the culture medium may not smoothly pass through the fiber web, death or proliferation of the cells migrated into the inner space may be reduced. In addition, when the average pore size is more than 50 µm, the migration of cells into the inner space of the fiber web and permeability of a culture medium may be good, but the cultured cells may be detached out of the fiber web together with the culture medium passing through the fiber web, and an increase in the detached cells which are cultured leads to difficult culture to a cell cluster having a desired three-dimensional shape.

In addition, the fiber web 100 may have a porosity of 40 to 90%, which is advantageous for more easily forming a cell cluster having a three-dimensional shape using cells migrated and proliferated into the fiber web, and loading a culture medium in pores in the fiber web or enhancing the permeability of a culture medium. If the porosity is less than 40%, it may be difficult to form a cell cluster having a three-dimensional shape, and it can lead to the death of cells migrated into the fiber web and proliferated. In addition, if the porosity is more than 90%, the scaffold may be disrupted during cell culture due to the reduced mechanical strength of the scaffold.

In addition, the fiber web 100 may have an average thickness of 1 to 100 µm, preferably 1 to 50 µm, and more preferably 1 to 20 µm. In addition, the fiber web 100 may have a basis weight of 0.1 to 30 $g/m^2$. If the fiber web has a thickness of less than 1 µm and/or a basis weight of more than 30 $g/m^2$, the inner space of the fiber web is smaller or the total volume is reduced, such that it may be difficult to culture a cell cluster having a three-dimensional shape and/or an amount of the cell clusters which can be obtained from the scaffold may be smaller. In addition, if the fiber web has a thickness of less than 1 µm and/or a basis weight of less than 0.1 $g/m^2$, the mechanical strength of the scaffold may be degraded. In addition, if the fiber web has a thickness of more than 100 µm, the permeability of a culture medium in a fiber web thickness direction may be degraded, and thus the cells cultured in the fiber web may be decreased in proliferation or may die.

In addition, a scaffold fiber 111 forming the above-described fiber web 100 may include, as a fiber-forming component, any one of known polymer compounds which can be formed in a fiber shape without limitation, and for example, includes a biodegradable component or a non-biodegradable component. When a biodegradable component is used as the material for the scaffold, the scaffold may be grafted into a body without a separate process of separation of cells cultured/proliferated/differentiated on the scaffold, the grafted scaffold may help the cultured cells in being well grafted into a body immediately after grafting, and since it can be biodegraded in the body after a certain period of time, a separate operation/treatment to remove the scaffold after grafting of the scaffold is not required, and thus the convenience of the treatment may be highly increased. In addition, since the material for the biodegradable component has high hydrophilicity and high degradability in water, water that can be used as a solution for dissolving the scaffold in a process of separating and harvesting the cultured cells by dissolving the scaffold using these properties has advantages such as causing almost no irritation to cells and not damaging the cultured cells physically/chemically.

In addition, when a non-biodegradable component is used as the material for the scaffold, due to a higher mechanical strength than that of the biodegradable scaffold fiber, cells may be stably cultured. In addition, since the degradation of the mechanical strength of the scaffold can be prevented by a culture solution, which comes into contact with the scaffold, applied in cell culture, cells may be more stably cultured. Moreover, since the it is very difficult to form a fiber web having a desired structure with the biodegradable component, compared with a non-biodegradable component, by electrospinning, in terms of handling and a stable spinning property, the non-biodegradable component is more preferable for easily producing a fiber web having desired pore size and porosity.

When a biodegradable fiber-forming component is included in the scaffold fiber 111, any compound known as a biocompatible component so as to minimize toxicity to cells and having biodegradability may be used without limitation. In addition, according to an exemplary embodiment of the present invention, the scaffold fiber has to have a nano-sized diameter, and to this end, the scaffold fiber may be produced by electrospinning. In this case, as the biodegradable fiber-forming component, a compound further having properties suitable for electrospinning is preferably used. As an example, the biodegradable fiber-forming component may include any one or more selected from the group consisting of polycaprolactone (PCL), polydioxanone (PDO), poly(L-lactide) (PLLA), poly(DL-lactide-co-glycolide) (PLGA), polyethylene oxide (PEO), polylactic acid (PLA) and polyvinyl alcohol (PVA), but the present invention is not limited thereto.

In addition, when a non-biodegradable fiber-forming component is included in the scaffold fiber 111, any compound known as a biocompatible component so as to minimize toxicity to cells and have non-biodegradability may be used without limitation. In addition, according to an exemplary embodiment of the present invention, the non-biodegradable scaffold fiber has to have a nano-sized diameter, and to this end, the scaffold fiber may be produced by electrospinning. In this case, as the non-biodegradable fiber-forming component, a compound further having properties suitable for electrospinning is preferably used. As an example, the non-biodegradable fiber-forming component may include any one or more selected from the group consisting of polystyrene, polyethylene terephthalate (PET), polyethersulfone (PES), polyvinylidene fluoride (PVDF), polydimethylsiloxane (PDMS), a polyamide, polyethylene, and a polyethyleneoxide-polypropyleneoxide block copolymer as a fiber-forming component, but the present invention is not limited thereto.

In addition, a diameter of the scaffold fiber can be determined to implement a pore size, a porosity, a basis weight, etc. by considering a cell size according to a type of desired culture cells, and thus the present invention is not particularly limited to the diameter. As an example, the scaffold fiber may have an average diameter of 10 nm to 100 μm, preferably 100 nm to 50 μm, more preferably 100 nm to 10 μm, and even more preferably 100 nm to 3 μm. If the scaffold fiber has an average diameter of less than 10 nm, the mechanical strength of the fiber web may be significantly degraded, and when the scaffold fiber has an average diameter of more than 100 μm, it may be difficult to produce a fiber web having porosity and a surface area of the scaffold fiber at desired levels.

Meanwhile, to three-dimensionally culture cells, the cells may be penetrated into and cultured in an inner space as well as on a surface of the scaffold 100, and one three-dimensional cell cluster may be ultimately formed by contacting the cells penetrated into and cultured in the inner space and the cells cultured on the surface. However, the cells cultured on the surface may also induce three-dimensional culture of cells due to the surface morphology of the scaffold for cell culture (or tissue engineering). As an example, the surface morphology of the scaffold for cell culture may not be smooth, but may have irregularities, thereby having a high surface roughness. The roughness of the surface morphology of the cell scaffold illustratively includes a plurality of concave and/or convex portions, and thus the cells may be more easily and firmly settled in spaces between the convex portions or grooves between the concave portions, in addition to the three-dimensional growth effect of the cells, such that the number of cells detached from the cell scaffold may be significantly reduced.

According to an exemplary embodiment of the present invention, to produce a scaffold for cell culture having the above-described surface morphology for enhancing the three-dimensional growth of cells and settlement of seeded cells, the fiber web may include a plurality of biodegradable scaffold fibers, and satisfy Conditions (1) and (2).

First, as Condition (1), a diameter dispersion coefficient (E) of the scaffold fibers may be 8 to 25%. The diameter dispersion coefficient (E) is a parameter that can estimate how close or wide the scaffold fibers are distributed compared with the average diameter, when a predetermined average diameter calculated in a distribution based on diameters of the scaffold fibers, and may be calculated by the following Mathematical Formula 3.

[Mathematical Formula 3]

Scaffold fiber diameter dispersion coefficient (%)=[(standard deviation for diameters of scaffold fibers (nm)/average diameter of scaffold fibers (nm))×100

The expression that the dispersion coefficient (%) according to Mathematical Formula 3 is 0% means that the standard deviation is 0, which means that the diameters of a plurality of scaffold fibers included in the fiber web all match the average diameter. On the contrary, a gradual increase in diameter dispersion coefficient means an increase in the number of scaffold fibers with larger and/or smaller diameters than the average diameter of the plurality of scaffold fibers included in the fiber web.

The scaffold according to an exemplary embodiment of the present invention satisfies that a dispersion coefficient relative to diameters of biodegradable scaffold fibers according to Condition (1) at a predetermined average diameter is 8 to 25%, thus, a compressed nanofiber web having an uneven surface morphology, when formed by arranging multiple concave portions and/or convex portions as described above, may be more easily formed. However, if the dispersion coefficient is excessively large, an increase in basis weight relative to a thickness may be high, and therefore, the average pore size and air permeability may be greatly reduced, and due to difficult inflow of a cell culture medium into the scaffold or difficult exchange thereof, cell culture may be difficult to perform in the scaffold and thus cell culture efficiency may be reduced. If the dispersion coefficient relative to a diameter is less than 8%, as the uniformity of diameters of the scaffold is increased, it is likely to express a smooth surface morphology and the uniformity of pore sizes also increases. However, when the seeded cells are cultured two-dimensionally along the surface, rather than three-dimensionally cultured, or the average diameter of the scaffold fiber is high, a pore structure having a large average pore size is generated, such that there is a concern that the seeded cells can be detached and a three-dimensional cell cluster cannot be cultured at a desired level. In addition, if the dispersion coefficient relative to a diameter is more than 25%, in a scaffold having a slightly smaller average diameter, due to increased non-uniformity of the scaffold diameter, the average pore size of the scaffold is very small, and therefore inflow of a cell culture medium into the scaffold or exchange thereof may be difficult, and cells may be cultured along the surface, rather than cultured three-dimensionally.

Next, as Condition (2), the air permeability of the fiber web may be 1 to 40 cfm. One of the major factors for three-dimensionally growing cells in the scaffold for cell culture is whether materials required for cell culture can be continuously and actively supplied. If cells are three-dimensionally grown on the surface of the scaffold for cell culture, it may be difficult to easily contact cells placed adjacent to the scaffold or cells cultured after penetration and settlement of the cells in an inner space of the scaffold for cell culture with a cell culture medium, compared with cells located at the exposed part of a cell cluster or cells located on the surface of the scaffold for cell culture. In addition, when the above-described material for the scaffold fiber is a biodegradable component, the biodegradable component may be degraded by continuous contact with moisture. However, when it is difficult for the moisture to permeate into the scaffold, degradation of the biodegradable component may be delayed, and therefore, it may be difficult to separate the cultured cell cluster having a three-dimensional shape from the scaffold.

Therefore, to prevent this, the air permeability of the fiber web may be 1 to 40 cfm. If the air permeability is less than 1.0 cfm, it may be difficult for cells to be penetrated into the scaffold, and permeation of a component that can dissolve the cell culture medium or the biodegradable component may not even be facilitated. In addition, if the air permeability is more than 40 cfm, a fiber web may have a significantly low mechanical strength, or the scaffold fiber may have a significantly large fineness, diameter and thickness. Therefore, the weight of the scaffold may increase, it may be difficult for the fiber web to be applied to an incubator with a limited small volume, and it may be difficult to culture the seeded cells to a desired amount due to detachment of the cells.

In addition, more preferably, the fiber web 100 may further satisfy Condition (3) and/or Condition (4).

First, as Condition (3) according to the present invention, in a diameter distribution of the biodegradable scaffold fibers, a value according to Mathematical Formula 1 may be 1.5 to 6.8, and therefore, cells seeded in the fiber web 100 may be more easily penetrated into the inner space of the fiber web, and the fiber web of the above-described scaffold having an uneven surface morphology may be more easily formed. For this reason, the scaffold may be more suitable for culture of a three-dimensional cell cluster.

[Mathematical Formula 1]

$$\frac{\text{Maximum diamter (nm)} - \text{Third quartile (nm)}}{\text{Third quartile (nm)} - \text{First quartile (nm)}}$$

In Mathematical Formula 1, "quartile" means a diameter of a scaffold fiber corresponding to a/4 of the four parts into which the total number of the biodegradable scaffold fibers, which is a total frequency, has been divided after a plurality of the biodegradable scaffold fibers included in the fiber web are arranged by diameter, the first quartile means a diameter of a scaffold fiber corresponding to ¼ of the total number of scaffold fibers in the diameter distribution, and the third quartile means a diameter of a scaffold fiber corresponding to ¾ of the total number of scaffold fibers in the diameter distribution. In one example, when the number of scaffold fibers is 15, a position of the first quartile means a scaffold fiber having the fourth largest diameter, and the first quartile means the diameter of the scaffold fiber at that time. Meanwhile, when the total number of scaffold fibers is 20, which is an even number, the first quartile position is between the fifth and sixth largest diameters, and the first quartile is calculated as the average of the fifth and sixth largest diameters.

As a value according to Mathematical Formula 1 for the first quartile, the third quartile and the maximum diameter value of a plurality of scaffold fibers included in the fiber web satisfies 1.5 to 6.8, seeded cells may be penetrated into the scaffold as well as being placed on the surface of the scaffold, it may be easy to implement an uneven surface morphology of the scaffold, and therefore, the scaffold may be suitable for culturing a three-dimensional cell cluster. If the value according to Mathematical Formula 1 is less than 1.5, there is a difficulty in culture of a desired three-dimensional cell cluster in which seeded cells may be two-dimensionally cultured on the surface of the scaffold for cell culture. In addition, if the value according to Mathematical Formula 1 is more than 6.8, the diameter distribution of the scaffold fiber may be too large to form a scaffold having a predetermined pore size, and the scaffold may have macropores such that seeded cells may be easily detached from the scaffold, resulting in difficult culture of a predetermined three-dimensional cell cluster. Here, the macropore refers to a pore having a diameter 10 times larger than the diameter of seeded cells.

In addition, as Condition (4) according to the present invention, since a value according to Mathematical Formula 2 may be 1.0 to 5.5 in the diameter distribution of the scaffold fibers, cells seeded in the fiber web 100 may be more easily penetrated into the inner space of the fiber web, the above-described fiber web having an uneven surface morphology of the scaffold may be more easily implemented, and thus the scaffold may be more suitable for culture of a three-dimensional cell cluster.

[Mathematical Formula 2]

$$\frac{\text{First quartile (nm)} - \text{Minimum diameter (nm)}}{\text{Third quartile (nm)} - \text{First quartile (nm)}}$$

If the value according to Mathematical Formula 2 is less than 1.0, the fiber web may have an even surface morphology, and there may be a difficulty in culture of a desired three-dimensional cell cluster in which seeded cells may be two-dimensionally cultured on the surface of the scaffold for cell culture. In addition, if the value according to Mathematical Formula 2 is more than 5.5, a diameter range between a scaffold fiber having the smallest diameter and a scaffold fiber corresponding to the first quartile position is widened, and therefore, the proportion of scaffold fibers having a small diameter may be increased. As a result, the proportion of pores having a small pore size may be increased, and thus there may be difficulty in culture of a desired three-dimensional cell cluster, such that the seeded cells are difficult to be penetrated and cultured in the scaffold for cell culture.

In addition, when a scaffold for cell culture is produced to satisfy both of the above-described Conditions (3) and (4), there are advantages of increasing migration into the fiber web and proliferation of the cells, three-dimensionally culturing cells on the surface or in the cells due to an uneven surface morphology, and promoting the culture of cells proliferated in the fiber web and thus preventing cell death due to increased permeability of a culture medium.

Meanwhile, the above-described fiber web 100 may further include a physiologically active component fixed to the surface of at least a part of the scaffold fibers. Here, the at least a part of the biodegradable scaffold fibers refers to a part of a single strand of the scaffold fiber and/or some of multiple strands of the scaffold fibers.

Cell culture technology that has been recently studied is developed for in vitro realization of an intercellular environment of an actual body, and to create a cell culture environment similar to the intercellular environment in the body, various components included in the extracellular matrix in the body tend to be contained in a culture medium in in vitro culture. However, when a material that can promote cell culture is contained in a culture medium, there is a limitation to continuous exposure of the material to cells that are being cultured, and for continuous exposure, a content of the material has to be increased in the culture medium, but there are problems in cost and proliferation efficiency. Accordingly, since a physiologically active component is included in a scaffold by being fixed to the surface of a scaffold fiber included in the fiber web according to an exemplary embodiment of the present invention, cell proliferation may be more accelerated by stabilizing adhesion of the physiologically active component to the cultured cells located on the scaffold fiber or in spaces around the scaffold fiber, and sustaining and amplifying cell stimulation and intracellular signal transduction thereby.

The physiologically active component may be a component inducing one or more of adhesion, migration, growth, proliferation and differentiation of cells.

First, an adhesive physiologically active component, which is a component of the physiologically active components, which enhances cell adhesion, may serve to fix cells to be cultured on a cell scaffold at an early stage to prevent suspension of the cells in a culture medium, and/or to fix a non-adhesive physiologically active component involved in the migration, growth, proliferation and differentiation of cells to a scaffold fiber to prevent detachment of the non-adhesive physiologically active component from the scaffold fiber during cell culture on the scaffold fiber. The adhesive physiologically active component may be any known adhesive component that does not exhibit cytotoxicity because it has biocompatibility, without limitation, and preferably includes one or more types selected from the group consisting of proteins comprising 1 to 20 repeats of amino acids of SEQ ID NOs: 1 to 7 and proteins produced by fusing at least two thereof, and therefore there are advantages of considerably decreasing cytotoxicity, having a high adhesive strength to the non-adhesive physiologically active component, and preventing detachment of the fixed non-adhesive physiologically active component and isolation of cells, which are caused by dissolving the adhesive physiologically active component in a culture medium during cell culture.

Figure 3A:
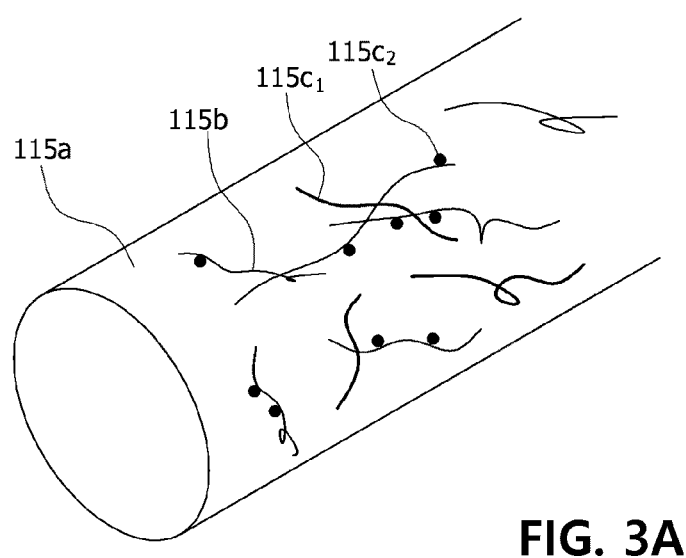
Figure 3B:
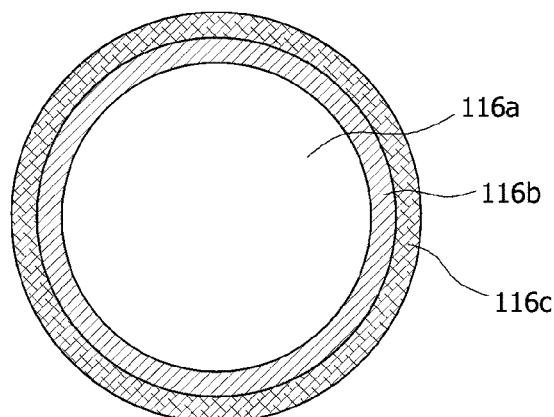

Meanwhile, as shown in FIG. 2A, an adhesive physiologically active component $111b_1$ may be fixed to the surface of a first scaffold fiber 111 consisting of a first fiber-forming component 111a. The adhesive physiologically active component may be fixed to the surface of the scaffold fiber while a part of the adhesive physiologically active component $111b_1$ is located in the scaffold fiber, and the other part of the adhesive physiologically active component $111b_1$ is located outside the fiber. Alternatively, as shown in FIG. 3A, an adhesive physiologically active component 115b may be fixed to a region of the outer surface of a fifth scaffold fiber 115, without location of an adhesive physiologically active component in the fifth scaffold fiber 115. Alternatively, as shown in FIG. 3B, the entire outer surface of a sixth scaffold fiber 116 may be coated with adhesive physiologically active components.

Subsequently, among physiologically active components which can be included in the fiber web, non-adhesive physiologically active components directly/indirectly inducing any one or more of migration, growth, proliferation and differentiation of cells to improve cell culture may be any known material that expresses the above-described function without limitation. For example, the physiologically active component may include any one or more among any one or more compounds selected from the group consisting of a monoamine, an amino acid, a peptide, a saccharide, a lipid, a protein, a glucoprotein, a glucolipid, a proteoglycan, a mucopolysaccharide and a nucleic acid, and a cell. Here, the monoamine includes, for example, a compound including a primary amine such as catecholamine or indole amine. In addition, the peptide may include an oligopeptide, and the protein may include a polypeptide, for example, fibronectin. The saccharide may include a monosaccharide, a polysaccharide, an oligosaccharide, and a carbohydrate. In addition, the lipid may be, for example, a steroid hormone.

Meanwhile, the physiologically active component may include a motif. The motif may be a natural or recombinant peptide comprising a predetermined amino acid sequence included in any one or more selected from proteins, glucoproteins and proteoglycans included in a growth factor or the ECM. Specifically, the motif may include a predetermined amino acid sequence included in any one or more growth factors (GFs) selected from the group consisting of adrenomedullin, angiopoietin, a bone morphogenetic protein (BMP), a brain-derived neurotrophic factor (BDNF), an epithelial growth factor (EGF), erythropoietin, a fibroblast growth factor, a glial cell line-derived neurotrophic factor (GDNF), a granulocyte colony-stimulating factor (G-CSF), a granulocyte macrophage colony-stimulating factor (GM-CSF), growth differentiation factor-9 (GDF9), a hepatocytic growth factor (HGF), a hepatoma-derived growth factor (HDGF), an insulin-like growth factor (IGF), a keratinocyte growth factor (KGF), a migration-stimulating factor (MSF), myostatin (GDF-8), a nerve growth factor (NGF), a platelet-derived growth factor (PDGF), thrombopoietin (TPO), a T-cell growth factor (TCGF), neuropilin, transforming growth factor-α (TGF-α), transforming growth factor-β (TGF-β), tumor necrosis factor-α (TNF-α), a vascular endothelial growth factor (VEGF), IL-1, IL-2, IL-3, IL-4, IL-5, IL-6 and IL-7. Alternatively, the motif may include a predetermined amino acid sequence included in any one or more selected from the group consisting of hyaluronic acid, heparin sulfate, chondroitin sulfate, dermatan sulfate, keratan sulfate, alginate, fibrin, fibrinogen, collagen, elastin, fibronectin, bitronectin, carderine and laminin in the ECM. In addition, the motif may include both of a predetermined amino acid sequence included in the growth factor and a predetermined amino acid sequence included in the ECM. More preferably, the motif may include one or more selected from the group consisting of proteins comprising amino acid sequences of SEQ. ID. NOs: 8 to 28 and one or more selected from the group consisting of proteins in which at least two of the proteins are fused, but the present invention is not limited thereto.

Meanwhile, the motif may be integrated with the above-described adhesive component by a covalent bond. For example, when the adhesive component is a protein, the motif may be covalently bonded to the N-terminus and/or the C-terminus of a polypeptide directly or via a heterologous peptide or polypeptide, and in this case, the physiologically active component may be more tightly adhered to a scaffold fiber, and release of the physiologically active component during cell culture may be minimized.

Figure 2B:
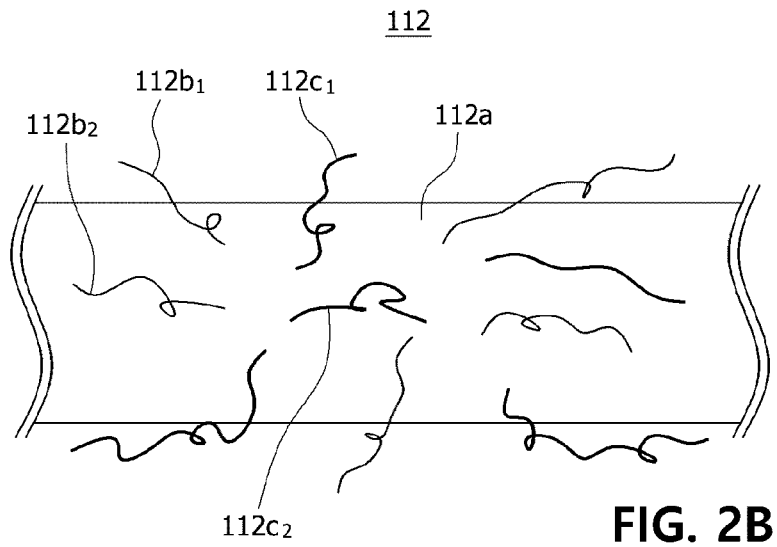
Figure 2C:
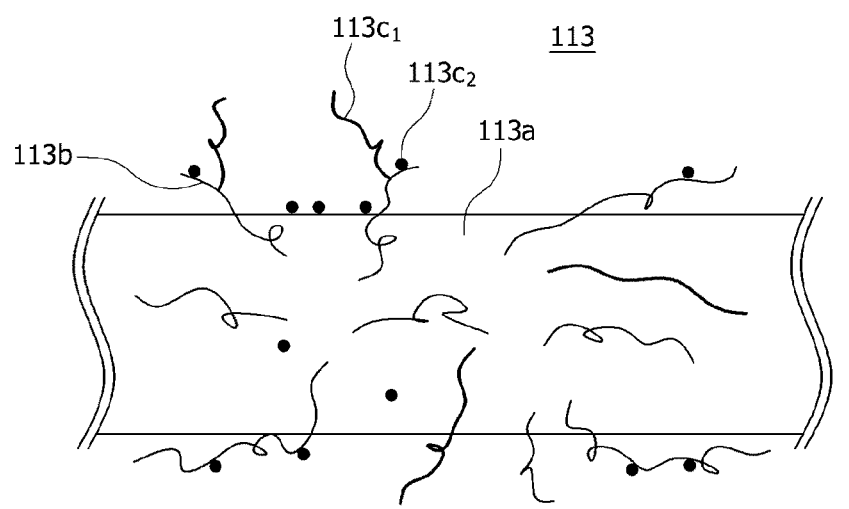
Figure 2D:
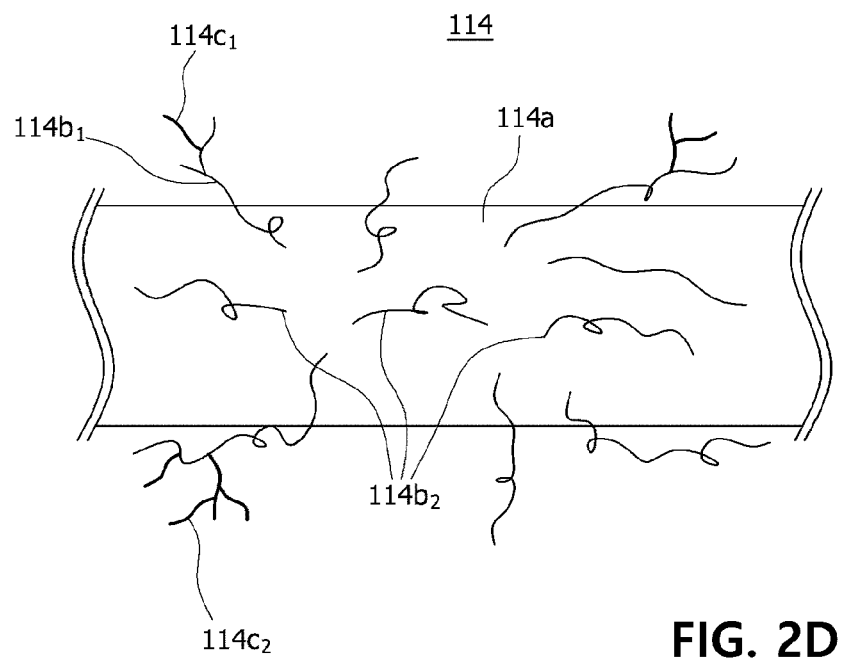

As shown in FIG. 2B, the above-described physiologically active component may be fixed to the surface of the scaffold fiber while a part of a physiologically active component $112c$ is located in the scaffold fiber and the other part of the physiologically active component $112c$ is located outside the fiber. In addition, as shown in FIGS. 2C and 2D, a physiologically active component $113c_1$, $113c_2$ or $114c_1$ may be fixed to a scaffold fiber 113 or 114 via an adhesive physiologically active component $113b$ or $114b_1$ fixed to the surface of the scaffold fiber 113 or 114 consisting of a fiber-forming component $113a$ or $114a$.

In addition, as shown in FIG. 3A, a physiologically active component $115c_1$ or $115c_2$ may be fixed to a part of the outer surface of the fifth scaffold fiber 115 via an adhesive physiologically active component $115b$ fixed to a region of the outer surface thereof, without location of an adhesive physiologically active component or physiologically active component in the fifth scaffold fiber 115. Alternatively, as shown in FIG. 3B, an adhesive physiologically active component $116b$ enclosing the entire outer surface of a sixth scaffold fiber 116 may be completely coated with a physiologically active component $116c$.

Meanwhile, as shown in FIGS. 2A to 2D, an adhesive physiologically active component $111b_2$, $112b_2$, $113b_1$ or $114b_2$ and/or a non-adhesive physiologically active component $112c_2$ may be further included in the scaffold fiber 111, 112, 113 or 114, respectively. The scaffold fiber including an adhesive component and/or a non-adhesive physiologically active component therein may be produced by spinning a mixture in which the adhesive physiologically active component and/or the non-adhesive physiologically active component is/are mixed with a biodegradable fiber-forming component in a spinning solution for producing a scaffold fiber. When the adhesive physiologically active component is included in the spinning step, detachment of the adhesive physiologically active component $111b_1$, $112b_1$, $113b_1$ or $114b_1$ from the scaffold fiber may be minimized by locating a part of the adhesive physiologically active component $111b_1$, $112b_1$, $113b_1$ or $114b_1$ in the scaffold fiber 111, 112, 113 or 114. In addition, when the non-adhesive physiologically active component is included in the spinning step, as shown in FIG. 2B, the non-adhesive physiologically active component $112c_1$ may be fixed to the scaffold fiber 112 without a separate adhesive physiologically active component.

A scaffold for cell culture or tissue engineering according to an exemplary embodiment of the present invention may include a monolayer of the above-described fiber web 100, or a stacked structure with a multilayer of the above-described fiber webs 100. In addition, a functional layer included in a conventional scaffold for cell culture/tissue engineering, for example, an adhesive layer for adhesion to a culture container may be also included at any surface.

A scaffold including the above-described fiber web may be produced by the following method. However, the present invention is not limited to this method.

The scaffold according to an exemplary embodiment of the present invention may be produced by (1) preparing a spinning solution containing a fiber-forming component; and (2) producing a fiber web formed by stacking scaffold fibers by electrospinning the spinning solution.

First, in Step (1), the spinning solution may include a solvent in addition to a fiber-forming component.

The solvent may be any one that is used in preparation of an electrospinning solution and can dissolve the above-described biodegradable or non-biodegradable fiber-forming component without limitation. In addition, if Step (2), which will be described below, is performed by dry spinning, a solvent that can be easily evaporated is preferably selected. Since the type of a solvent can be selected according to the type of a specifically selected biodegradable compound, the present invention is not particularly limited to a specific type of the solvent. In one example, the solvent may be any one or more selected from the group consisting of diethyl carbonate (DEC), dimethyl carbonate (DMC), ethyl methyl carbonate (EMC), propylene carbonate (PC), water, acetic acid, formic acid, chloroform, dichloromethane, acetone, 1,1,1,3,3,3-hexafluoro-2-propanol (HFIP) and isopropyl alcohol.

The spinning solution may be prepared by mixing the fiber-forming component and the solvent to have a viscosity of 50 to 3000 cps. If the viscosity of the spinning solution is less than 50 cps, due to high flowability of the spinning solution, it is difficult to produce a fiber web by spraying liquid drops from a nozzle of a sprayer, and when the viscosity of the spinning solution is more than 3000 cps, the flowability of the spinning solution may be lowered and thus the spinning property may be decreased.

In addition, the spinning solution may further include an additive included in a conventional scaffold for cell culture or scaffold for tissue engineering, and for example, the additive may be a hydrophilicity-enhancing component such as a non-ionic surfactant. Other than this, the additive may be a known one selected according to purpose, and therefore, in the present invention, descriptions of the additive will be omitted.

Meanwhile, the above-described spinning solution is described as a solution in which a fiber-forming component is dissolved in a solvent, but the present invention is not limited thereto. The spinning solution could be a melt in which a fiber-forming component is melted.

Subsequently, Step (2) is performed to produce a fiber web by electrospinning the above-described spinning solution.

Step (2) may be implemented using a conventional electrospinning device which may include a solution tank storing a spinning solution, and a spinning pack in which a plurality of spinning nozzles are linked to a high-voltage generator and arranged in a grid form. Meanwhile, a collector may be included under the spinning pack to collect a fiber mat in which spun scaffold fibers are stacked, and collect a continuous fiber mat having a predetermined thickness, which is located on a conveyer belt and sequentially formed. Here, as an external solidification solution is contained in the collector, the spun scaffold fibers may be solidified, or the spun scaffold fibers may be solidified in air or with separate cooling wind without an external solidification solution, and then the solidified scaffold fibers may be collected by the collector.

The collected scaffold fiber mat may be subjected to a drying process for evaporating the remaining solvent and the external solidification solution, and thereby the fiber web may be produced.

The produced fiber web may be also subjected to plasma treatment, coating of the surface of the scaffold fiber with dopamine, etc. to enhance hydrophilicity.

In addition, the produced fiber web may be further subjected to an elongation process in a specific direction for control of a pore size and orientation of the fiber-forming component forming the nanofiber. In addition, the fiber web may be further subjected to a process of applying heat and/or pressure to deepen a three-dimensional network structure and satisfy a basis weight with respect to a desired thickness, and this process may be a conventional calendering process. In addition, a process of forming a separate adhesive layer on one surface of the produced fiber web, for example, an edge of the fiber web may be further performed to fix or adhere the fiber web onto a culture container.

Meanwhile, according to an exemplary embodiment of the present invention, a fiber web further including an adhesive physiologically active component and/or a non-adhesive physiologically active component may be produced by, as a first method, spinning a mixture in which an adhesive physiologically active component and/or a non-adhesive physiologically active component is/are mixed in a spinning solution, prepared according to Step (1) of preparing a spinning solution, such that the adhesive physiologically active component and/or the non-adhesive physiologically active component is/are included in the scaffold fiber from the beginning. By the first method, a fiber web including a modified scaffold fiber as shown in FIGS. 2A to 2C may be produced.

In addition, as a second method, following the production of a fiber web in which an adhesive physiologically active component is included in a scaffold fiber from the beginning by spinning the mixture in which the adhesive physiologically active component is mixed in a spinning solution, prepared according to Step (1) of preparing a spinning solution, a different type of physiologically active component may be applied to the fiber web to be adhered to the adhesive physiologically active component fixed to the scaffold fiber. By the second method, a fiber web including a modified scaffold fiber as shown in FIG. 2D may be produced. Here, a method of applying the physiologically active component to the fiber web may be a conventional method, for example, immersion, spraying, electrodeposition.

In addition, as a third method, an adhesive physiologically active component is applied to the surface of a fiber web produced by the above-described Steps (1) and (2) to coat at least a part or all of the outer surface of the scaffold fiber 115 or 116 with an adhesive physiologically active component 115$b$ or 116$b$ as shown in FIG. 3A or 3B, and then the coated adhesive physiologically active component is coated with a non-adhesive physiologically active component 115$c_1$, 115$c_2$ or 116$c$, thereby producing a fiber web including a modified scaffold fiber.

As described above, a scaffold including the fiber web, along with a housing including the scaffold therein, may constitute a bioreactor. The bioreactor may further include a culture medium containing a variety of nutritional factors which affect cell proliferation or differentiation to proliferate and/or differentiate cells. The culture medium may be a conventional solution included in the bioreactor, and thus the present invention is not particularly limited thereto.

In addition, the bioreactor may further include an inlet through which the culture medium is put into the housing, and an outlet through which the culture medium is discharged to the outside. Alternatively, the bioreactor may have a closed housing which does not include an inlet/outlet connecting the outside with the inside of the housing. In addition, the bioreactor may further include other members which are included in a conventional bioreactor, and the present invention is not particularly limited thereto.

In addition, the scaffold according to an exemplary embodiment of the present invention may be included in a conventional culture container and serve as a cell incubator. The scaffold may be adhered to the inner surface of the culture container, or may be suspended in the culture medium included in the culture container.

In addition, the scaffold according to an exemplary embodiment of the present invention may include a cell cluster cultured on a region, which includes the outer surface and the inner space, of the fiber web in the scaffold to be used as a grafting kit. The grafting kit is preferably implemented by a scaffold formed of a biodegradable component, and in this case, the scaffold is biodegraded in a body without a separate operation for removing the scaffold after grafting, which makes the grafting easier. The grafting kit may further include other drugs that minimize immune rejection or help in engraftment of cells. Here, the cell cluster may include any one or more types of stem cells selected from the group consisting of totipotent stem cells, pluripotent stem cells, multipotent stem cells, oligopotent stem cells and single stem cells and/or one or more types of differentiated cells selected from the group consisting of hematopoietic stem cells, liver cells, fiber cells, epithelial cells, mesothelial cells, endothelial cells, muscle cells, nerve cells, immune cells, adipose cells, cartilage cells, bone cells, blood cells and skin cells.

Table 2 below is a table for the sequence listing which shows the amino acid sequences according to the sequence numbers described in the present invention.

TABLE 2

| SEQ. ID. NO: | Amino acid sequence |
|---|---|
| 1 | Met Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ser Ser Glu Glu Tyr Lys Gly Gly Tyr Tyr Pro Gly Asn Thr Tyr His Tyr His Ser Gly Gly Ser Tyr His Gly Ser Gly Tyr His Gly Gly Tyr Lys Gly Lys Tyr Tyr Gly Lys Ala Lys Lys Tyr Tyr Tyr Lys Tyr Lys Asn Ser Gly Lys Tyr Lys Tyr Leu Lys Lys Ala Arg Lys Tyr His Arg Lys Gly Tyr Lys Lys Tyr Tyr Gly Gly Ser Ser Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys |
| 2 | Met Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro |

TABLE 2-continued

| SEQ. ID. NO: | Amino acid sequence |
|---|---|
|  | Pro Thr Tyr Lys Ala Lys Pro Ser Tyr Pro Pro Thr Tyr Lys Ser Ser Glu Glu Tyr Lys Gly Gly Tyr Tyr Pro Gly Asn Thr Tyr His Tyr His Ser Gly Gly Ser Tyr His Gly Ser Gly Tyr His Gly Gly Tyr Lys Gly Lys Tyr Tyr Gly Lys Ala Lys Lys Tyr Tyr Lys Tyr Lys Asn Ser Gly Lys Tyr Lys Tyr Leu Lys Lys Ala Arg Lys Tyr His Arg Lys Gly Tyr Lys Lys Tyr Lys Gly Gly Ser Ser Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Gly Arg Gly Asp Ser Pro |
| 3 | Met Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Pro Trp Ala Asp Tyr Tyr Gly Pro Lys Tyr Gly Pro Pro Arg Arg Tyr Gly Gly Gly Asn Tyr Asn Arg Tyr Gly Arg Arg Tyr Gly Gly Tyr Lys Gly Trp Asn Asn Gly Trp Lys Arg Gly Arg Trp Gly Arg Lys Tyr Tyr Gly Tyr Ser Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Leu |
| 4 | Ala Asp Tyr Tyr Gly Pro Lys Tyr Gly Pro Pro Arg Arg Tyr Gly Gly Gly Asn Tyr Asn Arg Tyr Gly Arg Arg Tyr Gly Gly Tyr Lys Gly Trp Asn Asn Gly Trp Lys Arg Gly Arg Tip Gly Arg Lys Tyr Tyr |
| 5 | Ser Ser Glu Glu Tyr Lys Gly Gly Tyr Tyr Pro Gly Asn Thr Tyr His Tyr His Ser Gly Gly Ser Tyr His Gly Ser Gly Tyr His Gly Gly Tyr Lys Gly Lys Tyr Tyr Gly Lys Ala Lys Lys Tyr Tyr Lys Tyr Lys Asn Ser Gly Lys Tyr Lys Tyr Leu Lys Lys Ala Arg Lys Tyr His Arg Lys Gly Tyr Lys Lys Tyr Tyr Gly Gly Gly Ser Ser |
| 6 | Ala Lys Pro Ser Tyr Pro Pro Thr Tyr Lys |
| 7 | Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys |
| 8 | Arg Gly Asp |
| 9 | Arg Gly Asp Ser |
| 10 | Arg Gly Asp Cys |
| 11 | Arg Gly Asp Val |
| 12 | Arg Gly Asp Ser Pro Ala Ser Ser Lys Pro |
| 13 | Gly Arg Gly Asp Ser |
| 14 | Gly Arg Gly Asp Thr Pro |
| 15 | Gly Arg Gly Asp Ser Pro |
| 16 | Gly Arg Gly Asp Ser Pro Cys |
| 17 | Tyr Arg Gly Asp Ser |
| 18 | Ser Pro Pro Arg Arg Ala Arg Val Thr |
| 19 | Trp Gln Pro Pro Arg Ala Arg Ile |
| 20 | Asn Arg Trp His Ser Ile Tyr Ile Thr Arg Phe Gly |
| 21 | Arg Lys Arg Leu Gln Val Gln Leu Ser Ile Arg Thr |
| 22 | Lys Ala Phe Asp Ile Thr Tyr Val Arg Leu Lys Phe |
| 23 | Ile Lys Val Ala Asn |
| 24 | Lys Lys Gln Arg Phe Arg His Arg Asn Arg Lys Gly Tyr Arg Ser Gln |
| 25 | Val Ala Glu Ile Asp Gly Ile Gly Leu |
| 26 | Pro His Ser Arg Asn Arg Gly Asp Ser Pro |

TABLE 2-continued

| SEQ. ID. NO: | Amino acid sequence |
|---|---|
| 27 | Asn Arg Trp His Ser Ile Tyr Ile Thr Arg Phe Gly |
| 28 | Thr Trp Tyr Lys Ile Ala Phe Gln Arg Asn Arg Lys |

EXAMPLE

Hereinafter, the present invention will be described in further detail with reference to examples. The examples are merely provided to more fully describe the present invention, and it will be obvious to those of ordinary skill in the art that the scope of the present invention is not limited to the following examples.

Example 1

First, to prepare a spinning solution, 12 g of polyvinylidene fluoride (Arkema, Kynar761) as a fiber-forming component was dissolved in 88 g of a mixed solvent prepared by mixing dimethylacetamide and acetone at a weight ratio of 70:30 using a magnetic bar at 80° C. for 6 hours, thereby preparing a mixed solution. A fiber web having a thickness of 5.5 μm and a weight of 5g/m$^2$, which is a scaffold for cell culture shown in Table 3 below, was obtained by electrospinning of the prepared spinning solution using an electrospinning device under conditions of an applied voltage of 25kV, a distance between a current collector and a spinning nozzle of 25 cm and a discharge amount of 0.05 ml/hole under an environment of R.H. 65% and 30° C. A scaffold fiber forming the fiber web had an average diameter of 693.9 nm, and a standard deviation for diameters of the scaffold fibers was 86.0 nm, the smallest one of the diameters of the scaffold fibers was 350.0 nm, the first quartile (Q1) was 644.0 nm, the third quartile (Q3) was 739.0 nm, and the largest one of the diameters of the scaffold fibers was 1294.0 nm.

Examples 2 to 12

A scaffold for cell culture having a fiber web shown in Table 3 or 4, which has a diameter distribution of a scaffold fiber included in the fiber web produced as shown in Table 3 or 4, was obtained in the same manner as described in Example 1 by controlling a concentration of a PVDF component in a spinning solution.

Experimental Example 1

The following physical properties of the fiber webs produced in Examples were evaluated and shown in Table 3 below.

1. Diameter Distribution of Scaffold Fiber in Fiber Web

Figure 4:
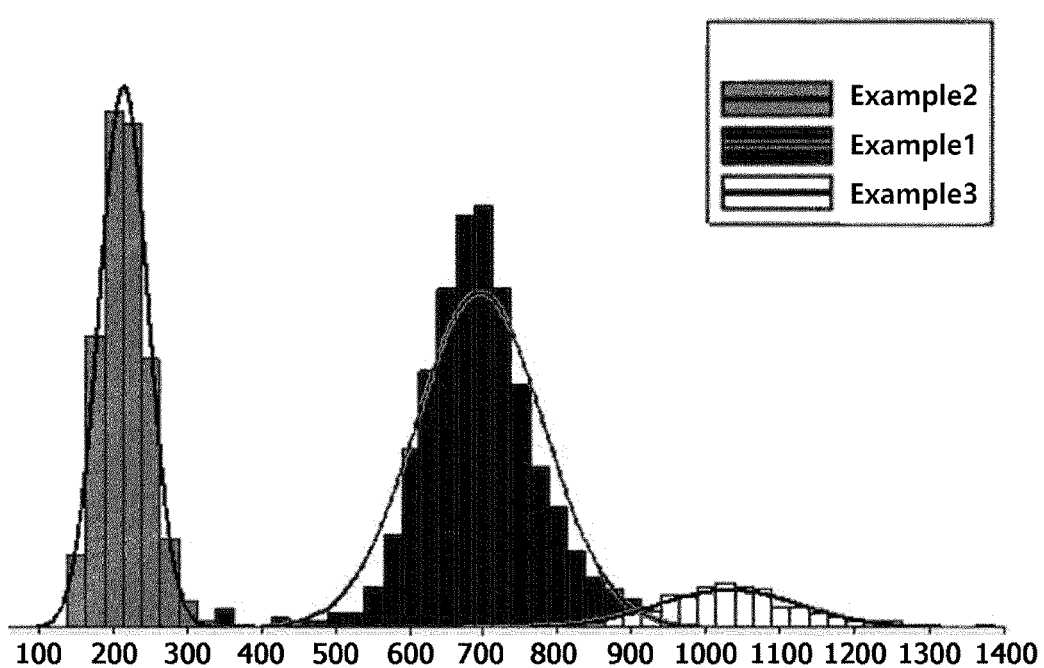
FIG. 4 is a graph showing that the fiber diameter distribution of scaffold fibers included in an exemplary embodiment of the present invention is expressed as the cumulative number of the scaffold fibers per diameter.

An average, standard deviation, the first quartile (Q1) and the third quartile (Q3), and the above-described Mathematical Formulas 1 and 2 were calculated using the diameter distribution of a scaffold fiber, measured by a method according to a fiber diameter program (developed by AMOGREENTECH Co., Ltd.). In addition, the cumulative number of scaffold fibers per diameter was determined according to the diameter distribution of the scaffold fibers measured in Examples 1 to 3, and is shown in the graph of FIG. 4.

2. Air Permeability of Fiber Web

Air permeability was determined using a device produced by TEXTEST Instruments after cutting the fiber web to a test area of 38 cm$^2$ to be placed in the device, and blowing air at a test pressure of 125 Pa to measure an amount of air passing through the fiber web, and the unit of the air permeability was cfm (ft3/ft2/min).

3. Scanning Electron Microscope (SEM) Imaging for Fiber Web

Figure 5:
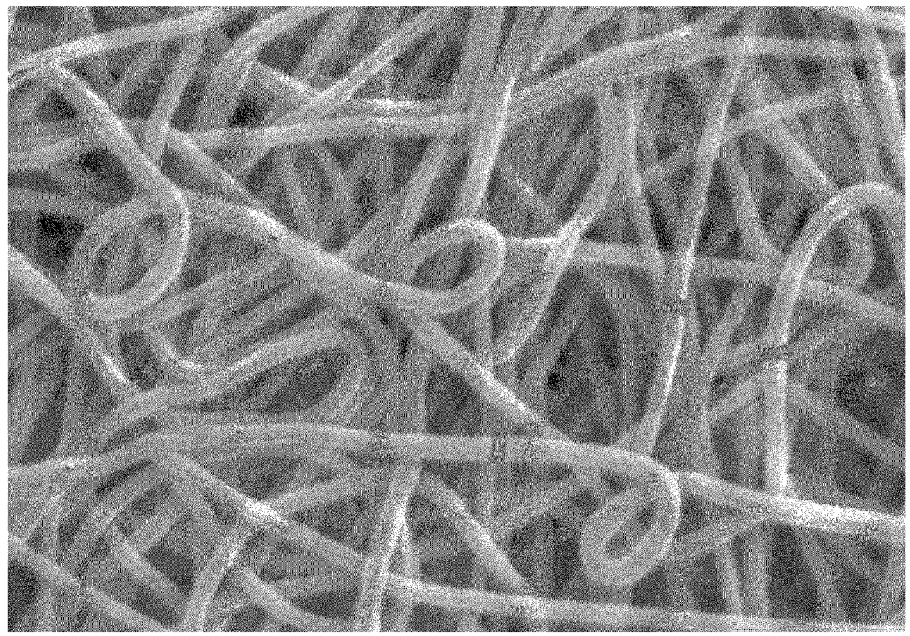
FIGS. 5 to 7 are scanning electron microscope (SEM) images of a fiber web included in an exemplary embodiment of the present invention.
Figure 6:
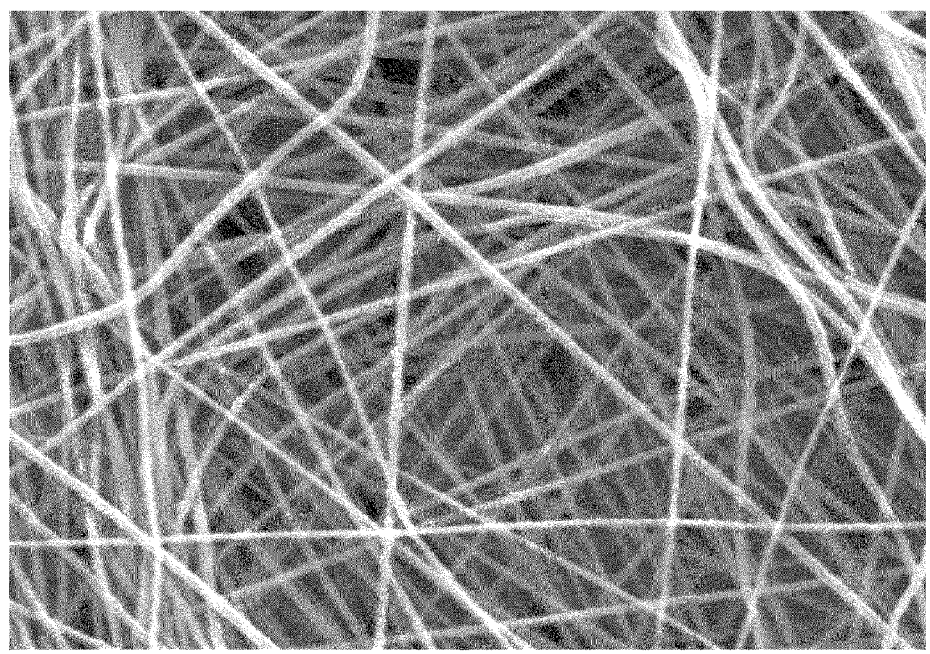
Figure 7:
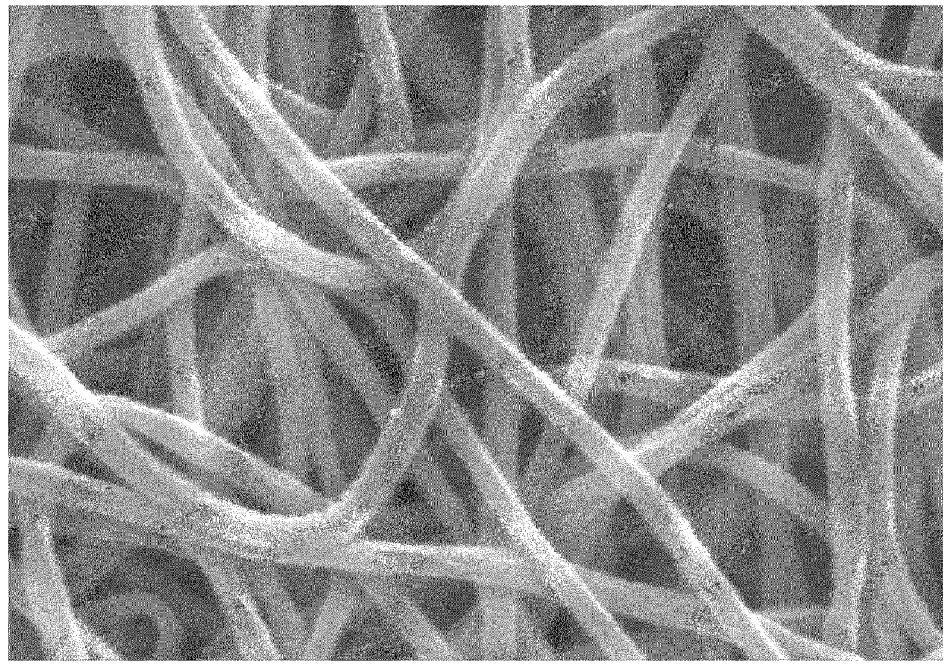

SEM imaging was performed on the fiber webs according to Examples 1 to 3, and the results are shown in FIGS. 5 to 7.

Experimental Example 2

The fiber webs produced in the examples were cut to the same size, and then fixed on well plates for cell culture. Mesenchymal stem cells (MSC) were loaded in the well plates containing the fiber web at 5×10$^4$ cells/cm$^2$, fetal bovine serum (FBS) was added to a medium prepared by mixing 2 ml of KSB-3 supplements (S2901) to 500 ml of KBS-3 basal medium (B1001) to be 10% of the total weight of the medium, and the cells were proliferated in a medium containing penicillin/streptomycin at 1/100 of the total volume of the medium at 37 □ for 4 days.

Afterward, the cultured MSC were stained using a cell counting kit 8 (CCK-8), and absorbance was measured using an UV-vis spectrometer. Here, as the control, MSCs two-dimensionally cultured in a cell culture dish under the same culture conditions used above were used.

Among the measured absorbances of the examples, based on the absorbance of Example 1, which is set to 100%, the absorbances of the other examples are relatively shown in Table 3 or 4.

As the absorbance is higher, it can be evaluated that cells were well cultured after the cells were settled on the scaffold for cell culture was settled.

Experimental Example 3

All procedures were carried out in the same manner as used in Experimental Example 1 to prepare well plates containing a fiber web. Fibroblasts (HS27) were loaded in the prepared well plates, and proliferated in 10% complete media at 37 □ for 4 days. Here, the 10% complete media was prepared by mixing Ham's F12 medium with Dulbecco Modified Eagle Medium (DMEM) in a volume ratio of 1:1.5, and adding 7 vol % of FBS, 65 U/mL of penicillin and 65 μg/mL of streptomycin.

Afterward, the culture fibroblasts (HS27) were stained using CCK-8, and absorbance was measured using an UV-vis spectrometer. Here, as the control, HS27s two-dimensionally cultured in a cell culture dish under the same culture conditions used above were used. Among the measured absorbances of the examples, based on the absorbance of Example 1, which is set to 100%, the absorbances of the other examples are relatively shown in Table 3 or 4.

Figure 8:
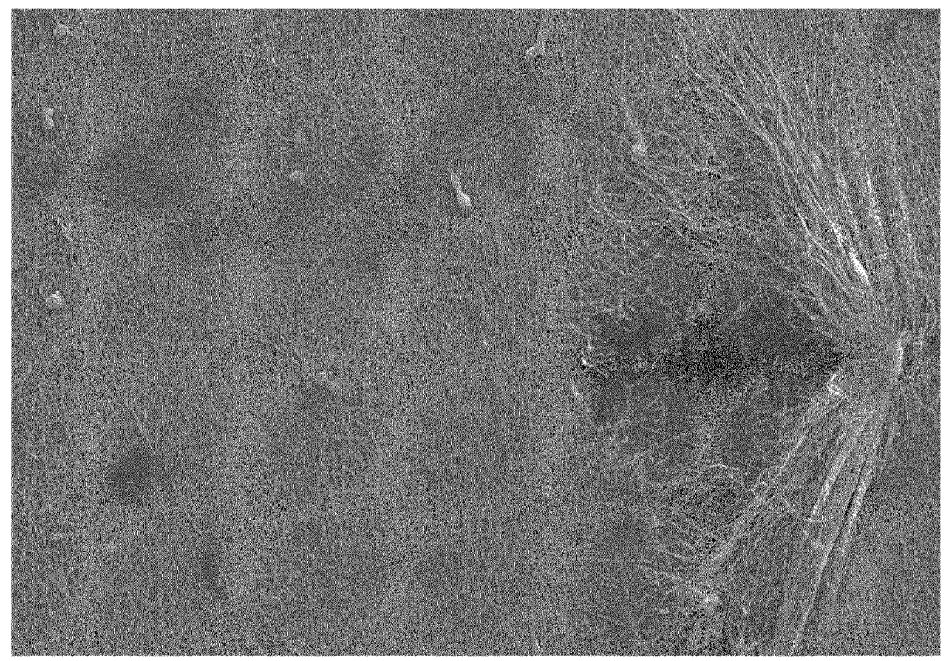
FIGS. 8 and 9 are SEM images of fibroblasts cultured for one day on a scaffold for cell culture according to an exemplary embodiment of the present invention.
Figure 9:
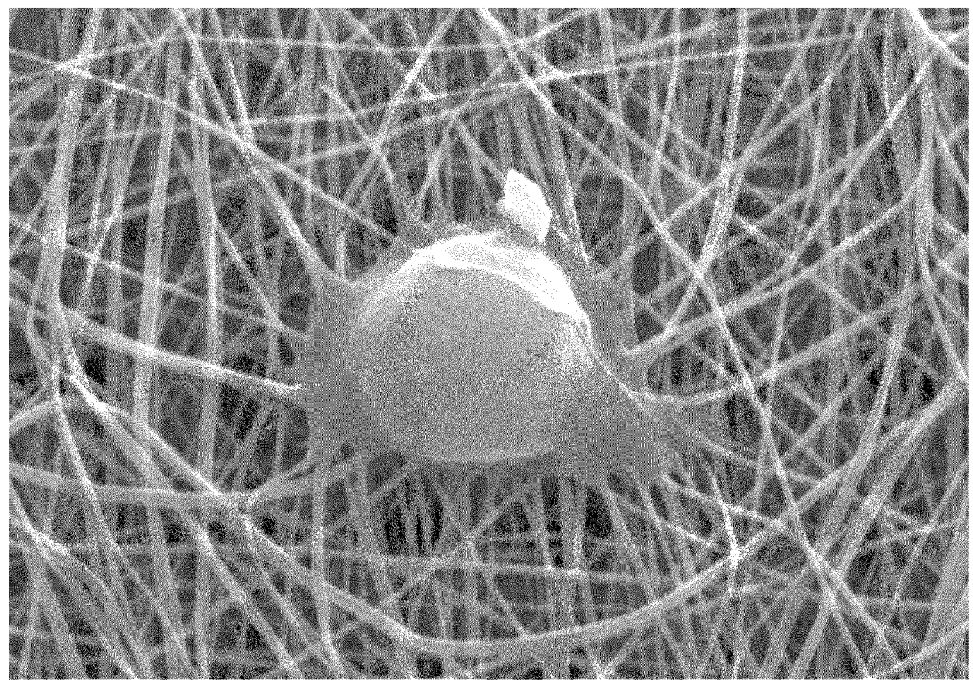

In addition, one day after fibroblasts were seeded on the scaffold for cell culture according to Example 2, SEM imaging was performed on the proliferated fibroblasts, and the results are shown in FIGS. 8 (×500) and 9 (×8000).

a more even surface of the scaffold since the scaffold is produced with scaffold fibers having a small average diameter, which is expected to result in creation of a culture environment more suitable for fibroblasts than stem cells.

TABLE 3

|  |  | Example 1 | Example 2 | Example 3 | Example 4 | Example 5 | Example 6 |
|---|---|---|---|---|---|---|---|
| Fiber web | Average diameter (nm) | 693.9 | 214.4 | 1029.9 | 598.5 | 601.6 | 612.2 |
|  | Standard deviation for diameter (nm) | 86.0 | 32.7 | 96.7 | 128.4 | 138.5 | 156.3 |
|  | Minimum diameter (nm) | 350.0 | 140.0 | 740.0 | 225.0 | 228.5 | 190.5 |
|  | First quartile (Q1, nm) | 644.0 | 192.0 | 964.3 | 546.0 | 532.4 | 502.7 |
|  | Third quartile (Q1, nm) | 739.0 | 234.0 | 1081.0 | 689.0 | 750.1 | 790.4 |
|  | Maximum Diameter (nm) | 1294.0 | 472.0 | 1385.0 | 1364.0 | 1465.4 | 1430.4 |
|  | Dispersion coefficient (%) | 12.39 | 15.25 | 9.39 | 21.45 | 23.02 | 25.53 |
|  | Mathematical Formula 1 | 5.84 | 5.67 | 2.60 | 4.72 | 3.29 | 2.22 |
|  | Mathematical Formula 2 | 3.09 | 1.24 | 1.92 | 2.24 | 1.40 | 1.09 |
|  | Basis weight (g/m$^2$) | 5.0 | 3.8 | 4.7 | 5.2 | 5.4 | 5.6 |
|  | Thickness (μm) | 5.5 | 5.2 | 5.5 | 5.5 | 5.5 | 5.5 |
|  | Air permeability (cfm) | 6.22 | 2.84 | 23.00 | 6.80 | 3.65 | 2.44 |
| Culture result | Relative absorbance for stem cells (%) | 100 | 97.6 | 109.1 | 103.1 | 97.3 | 89.6 |
|  | Relative absorbance for fibroblasts (%) | 100 | 111.4 | 99.3 | 100 | 96.7 | 94.2 |

TABLE 4

|  |  | Example 7 | Example 8 | Example 9 | Example 10 | Example 11 | Example 12 |
|---|---|---|---|---|---|---|---|
| Fiber web | Average diameter (nm) | 1018.9 | 1408.4 | 1227.0 | 1230.0 | 620.4 | 680.0 |
|  | Standard deviation for diameter (nm) | 68.8 | 116.0 | 108.0 | 110.1 | 90.4 | 120.4 |
|  | Minimum diameter (nm) | 774.7 | 1117.5 | 870.4 | 808.0 | 330.0 | 333.0 |
|  | First quartile (Q1, nm) | 989.0 | 1334.0 | 1169.4 | 1153.3 | 560.4 | 628.0 |
|  | Third quartile (Q1, nm) | 1075.4 | 1621.0 | 1373.0 | 1310.0 | 659.0 | 740.0 |
|  | Maximum Diameter (nm) | 1355.0 | 1883.0 | 1662.0 | 1555.0 | 1305.0 | 1550.0 |
|  | Dispersion coefficient (%) | 6.75238 | 8.236297 | 8.801956 | 8.95122 | 14.57124 | 17.70588 |
|  | Mathematical Formula 1 | 3.236111 | 0.912892 | 1.41945 | 1.563497 | 6.551724 | 7.232143 |
|  | Mathematical Formula 2 | 2.480324 | 0.754355 | 1.468566 | 2.203574 | 2.336714 | 2.633929 |
|  | Basis weight (g/m$^2$) | 4.5 | 4.3 | 4.5 | 4.5 | 5.0 | 5.2 |
|  | Thickness (μm) | 5.5 | 5.6 | 5.5 | 5.5 | 5.4 | 5.6 |
|  | Air permeability (cfm) | 32.64 | 42.61 | 30.66 | 37.13 | 5.65 | 6.32 |
| Culture result | Relative absorbance for stem cells (%) | 90.0 | 89.6 | 97.1 | 106.9 | 104.3 | 97.5 |
|  | Relative absorbance for fibroblasts (%) | 91.5 | 90.1 | 95.5 | 98.2 | 98.3 | 96.5 |

As seen from Tables 3 and 4, Example 2 shows that the relative absorbance for the fibroblasts is significantly increased, compared with that of Example 1, this is due to In addition, Example 3 shows that the relative absorbance for stem cells was significantly increased, compared with that of Example 1, this is due to a less even surface of the scaffold since the scaffold is produced with a fiber having a larger average diameter than that of Example 1, which is expected to result in creation of a culture environment more suitable for stem cells.

Meanwhile, in Examples 1 and 4 to 6, although scaffolds are formed with scaffold fibers having a similar average diameter, after cells are seeded and cultured, it can be confirmed that relative absorbance is greatly decreased, and particularly, the absorbance for stem cells is highly decreased in Example 6 in which the dispersion coefficient with respect to a diameter is beyond the preferred range according to the present invention, compared with Examples 1, 4 and 5.

In addition, referring to Examples 3 and 9 to 12 in terms with Mathematical Formula 1 according to the present invention, it can be confirmed that the relative absorbance for fibroblasts is decreased, and particularly, the relative absorbance for stem cells is reduced in Example 9, compared with Examples 3 and 10. In addition, it can be confirmed that relative absorbances for fibroblasts and stem cells are also decreased in Example 12, compared with Examples 3 and 11.

Although exemplary embodiments of the present invention have been described above, the spirit of the present invention is not limited to the exemplary embodiments presented herein, and it will be understood by those of ordinary skill in the art that other exemplary embodiments may be easily suggested by adding, changing, deleting or adding components within the scope of the same idea and also included in the scope of the spirit of the present invention.

The invention claimed is:

1. A scaffold for cell culture or tissue engineering, comprising:
- a fiber web formed of a plurality of scaffold fibers, the scaffold fibers having a three-dimensional network structure,
- wherein the scaffold fibers have an average diameter of 214.4 nm to 1230.0 nm, and
- wherein the fiber web satisfies the following Conditions (1) to (3):
  - (1) in a diameter distribution of the scaffold fibers, a diameter dispersion coefficient (E) of the scaffold fibers is 8.95122 to 21.45%,
  - (2) an air permeability of the fiber web is 1 to 40 cfm, and
  - (3) in the diameter distribution of the scaffold fibers, a value according to Mathematical Formula 1 is 1.5 to 6.8:

[Mathematical Formula 1]

$$\frac{\text{Maximum diamter (nm)} - \text{Third quartile (nm)}}{\text{Third quartile (nm)} - \text{First quartile (nm)}}.$$

2. The scaffold according to claim 1, wherein the fiber web has an average pore size of 0.05 to 10 μm and a porosity of 40 to 90 %.

3. The scaffold according to claim 1, wherein the fiber web has a thickness of 1 to 20 μm and a basis weight of 1 to 30 g/m².

4. The scaffold according to claim 1, wherein the scaffold fibers further include a physiologically active component inducing any one or more of adhesion, migration, growth, proliferation and differentiation of cells on an outer surface thereof.

5. The scaffold according to claim 4, wherein the physiologically active component includes any one or more among any one or more compounds selected from the group consisting of a monoamine, an amino acid, a peptide, a saccharide, a lipid, a protein, a glucoprotein, a glucolipid, a proteoglycan, a mucopolysaccharide and a nucleic acid, and a cell.

6. The scaffold according to claim 4, wherein the scaffold fibers are produced by spinning a spinning solution containing the physiologically active component.

7. The scaffold according to claim 1, wherein the fiber web further satisfies the following Condition (4) in the diameter distribution of the scaffold fibers:

(4) a value according to Mathematical Formula 2 is 1.0 to 5.5:

$$\frac{\text{First quartile (nm)} - \text{Minimum diameter (nm)}}{\text{Third quartile (nm)} - \text{First quartile (nm)}}.$$ [Mathematical Formula 2]

8. The scaffold according to claim 1, wherein the scaffold fibers include any one or more biodegradable components selected from the group consisting of polycaprolactone (PCL), polydioxanone (PDO), poly(L-lactide) (PLLA), poly (DL-lactide-co-glycolide) (PLGA), polyethylene oxide (PEO), polylactic acid (PLA) and polyvinyl alcohol (PVA) as a fiber-forming component.

9. The scaffold according to claim 1, wherein the scaffold fibers include any one or more non-biodegradable components selected from the group consisting of polystyrene, polyethylene terephthalate (PET), polyethersulfone (PES), polyvinylidene fluoride (PVDF), polydimethylsiloxane (PDMS), a polyamide, polyethylene and a polyethyleneoxide-polypropyleneoxide block copolymer as a fiber-forming component.

10. A bioreactor comprising:
the scaffold according to claim 1; and
a housing having the scaffold therein.

11. A grafting kit, comprising:
the scaffold according to claim 1; and
a cell cluster cultured in outer and inner spaces of the fiber web of the scaffold.

12. The kit according to claim 11, wherein the cell cluster includes any one or more types of stem cells selected from the group consisting of totipotent stem cells, pluripotent stem cells, multipotent stem cells, oligopotent stem cells and single stem cells, and/or one or more types of differentiated cells selected from the group consisting of hematopoietic stem cells, liver cells, fiber cells, epithelial cells, mesothelial cells, endothelial cells, muscle cells, nerve cells, immune cells, adipose cells, cartilage cells, bone cells, blood cells and skin cells.

* * * * *